(12) United States Patent
Warren

(10) Patent No.: US 7,983,749 B2
(45) Date of Patent: Jul. 19, 2011

(54) CARDIAC RHYTHM MANAGEMENT SYSTEM WITH TIME-DEPENDENT FREQUENCY RESPONSE

(75) Inventor: Jay A. Warren, San Juan Capistrano, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1376 days.

(21) Appl. No.: 10/615,636

(22) Filed: Jul. 10, 2003

(65) Prior Publication Data

US 2004/0167578 A1 Aug. 26, 2004

(51) Int. Cl.
*A61N 1/362* (2006.01)
(52) U.S. Cl. .......................................................... 607/9
(58) Field of Classification Search ........................ 607/9
See application file for complete search history.

(56) References Cited

U.S. PATENT DOCUMENTS

| | | | |
|---|---|---|---|
| 3,569,852 A | 3/1971 | Berkovits | 330/132 |
| 3,885,552 A | 5/1975 | Kennedy | 128/2.05 R |
| 4,281,664 A | 8/1981 | Duggan | 128/696 |
| 4,298,007 A | 11/1981 | Wright et al. | 128/419 G |
| 4,365,639 A | 12/1982 | Goldreyer | 128/786 |
| 4,381,786 A | 5/1983 | Duggan | 128/419 PG |
| 4,408,615 A | 10/1983 | Grossman | 128/696 |
| 4,418,695 A | 12/1983 | Buffet | 128/419 PG |
| 4,436,093 A | 3/1984 | Belt | 128/419 PG |
| 4,494,551 A | 1/1985 | Little, III et al. | 128/696 |
| RE32,361 E | 2/1987 | Duggan | 128/696 |
| 4,665,919 A | 5/1987 | Mensink et al. | 128/419 PG |
| 5,003,976 A | 4/1991 | Alt | 128/419 PG |
| 5,024,221 A | 6/1991 | Morgan | 128/419 |
| 5,074,303 A | 12/1991 | Hauck | 128/419 |
| 5,107,849 A | 4/1992 | Bellin et al. | 128/696 |
| 5,111,815 A | 5/1992 | Mower | 128/419 |
| 5,161,529 A * | 11/1992 | Stotts et al. | 607/27 |
| 5,162,991 A | 11/1992 | Chio | 364/413.03 |
| 5,179,947 A | 1/1993 | Meyerson et al. | 128/419 PG |
| 5,253,644 A | 10/1993 | Elmvist | 607/14 |
| 5,259,387 A | 11/1993 | dePinto | 128/696 |
| 5,282,840 A | 2/1994 | Hudrlik et al. | 607/28 |
| 5,309,917 A * | 5/1994 | Wang et al. | 600/508 |
| 5,357,969 A | 10/1994 | Herleikson | 128/696 |
| 5,405,364 A | 4/1995 | Noren et al. | 607/17 |
| 6,185,450 B1 * | 2/2001 | Seguine et al. | 600/509 |

FOREIGN PATENT DOCUMENTS

| | | |
|---|---|---|
| EP | 0372698 A1 | 6/1990 |
| WO | WO-0053258 A1 | 9/2000 |

OTHER PUBLICATIONS

"International Search Report—PCT/US00/06090", 4 pages.

* cited by examiner

*Primary Examiner* — Niketa I Patel
*Assistant Examiner* — Alyssa M Alter
(74) *Attorney, Agent, or Firm* — Schwegman, Lundberg & Woessner, P.A.

(57) ABSTRACT

A cardiac rhythm management system includes a time-dependent frequency response for sensed heart signals. A change in the frequency response of a sensing circuit is triggered by a sensed or evoked event to make it less sensitive to the detection of a subsequent event for a period of time. For example, a passband bandwidth is reduced, then increased during the time period triggered by the event. For even more event-triggered selectivity, a gain is reduced, then increased during the time period triggered by the event. This provides better discrimination between particular events included in a heart signal so that appropriate therapy can be delivered to the patient based such events.

31 Claims, 19 Drawing Sheets

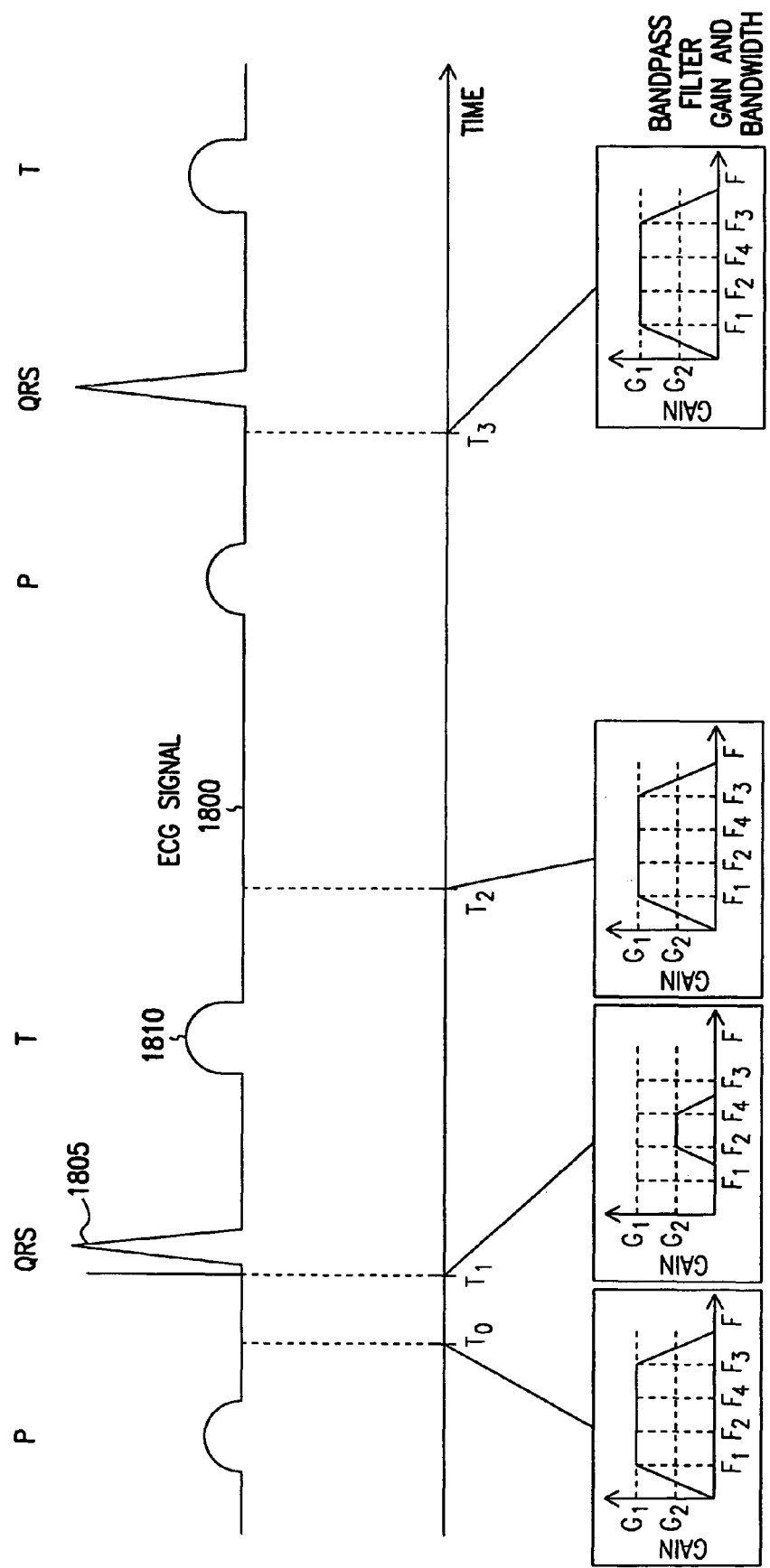

CARDIAC RHYTHM MANAGEMENT SYSTEM WITH TIME-DEPENDENT FREQUENCY RESPONSE

CROSS-REFERENCE TO RELATED APPLICATIONS

This application claims the benefit of priority under 35 U.S.C. §365(c) and §120 to International Application Number PCT/US00/06090, filed Mar. 9, 2000 and under 35 U.S.C. §119(e) to U.S. application No. 60/124,100 filed Mar. 12, 1999, both of which are hereby incorporated by reference herein.

TECHNICAL FIELD

This invention relates generally to cardiac rhythm management systems and particularly, but not by way of limitation, to a cardiac rhythm management system with a time-dependent frequency response for sensed heart signals.

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management devices is the sensing of intrinsic heart signals. These electrical signals, which are commonly viewed on an electrocardiograph (ECG) display monitor, are produced by the body itself, and include depolarizations that result in heart contractions. For example, a sinoatrial node provides depolarization impulses, referred to as P-waves, that are normally conducted through atrial tissue, resulting a contraction of the atrial chamber of the heart. Such conducted atrial impulses normally reach the atrioventricular node, which then normally provides a resulting ventricular depolarization impulse, referred to as a QRS complex, that is conducted through the ventricular tissue, resulting in a contraction of the ventricular chamber of the heart. The intrinsic heart signals also include repolarizations, such as a T-wave that is generated as the ventricle relaxes and fills with blood before its next contraction. Thus, heart signals include various "events," including depolarizations (e.g., P-waves and QRS complexes), and also including repolarizations (e.g., T-waves).

It is important for a cardiac rhythm management device to be capable of distinguishing between various events sensed on such intrinsic heart signals, in order to ensure that appropriate therapy is delivered to the patient based on the sensed intrinsic heart signal. However, certain events, such as depolarizations and repolarizations, include similar frequency contents, making discrimination between these events difficult. There is a need for improved techniques of sensing intrinsic heart signals.

SUMMARY

This document describes, among other things, a cardiac rhythm management system with a time-dependent frequency response for sensed heart signals. A change in the frequency response is triggered by a sensed or evoked event to make it less sensitive to the detection of a subsequent event for a period of time. This provides better discrimination between particular events included in a heart signal so that appropriate therapy can be delivered to the patient based such events.

In one embodiment, the cardiac rhythm management system includes a sensing circuit for sensing a heart signal, the sensing circuit having a frequency response that is time-dependent during a first time period initiated by one of an evoked or an intrinsic event of the heart signal.

In another embodiment, the cardiac rhythm management system, includes an electronics unit. The electronics unit includes a therapy circuit, a sensing circuit for sensing a heart signal of a heart, and a bandpass filter, included in the sensing circuit. The bandpass filter includes a frequency response that is time-dependent during a first time period initiated by one of an evoked or an intrinsic event of the heart signal. A leadwire is coupled to the electronics unit. A programmer, remote from and communicatively coupled to the electronics unit, includes a parameter controlling one of: (a) the frequency response of the bandpass filter, and (b) the duration of the first time period.

In another embodiment, the cardiac rhythm management system includes the following method. A heart signal that includes an intrinsic event is received from a heart. The heart signal is filtered to attenuate frequencies outside a frequency range having a first frequency range value. The event is detected. The frequency range is adjusted from the first frequency range value to a second frequency range value in response to the detection of the event.

In another embodiment, the cardiac rhythm management system includes the following method. A heart signal that includes an intrinsic event is received from a heart. A stimulation is provided to the heart for obtaining an evoked event. The heart signal is filtered to attenuate frequencies outside a first frequency range value. The intrinsic event is detected. The frequency range is narrowed from the first frequency range value to a second frequency range value in response to (a) the detection of the intrinsic event, and (b) the providing the stimulation. The frequency range is widened from the second frequency range value, such that the frequency range approaches the first frequency range value after a first time period from (a) the detection of the intrinsic event and (b) the providing the stimulation. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

FIG. 20 is a signal flow graph, corresponding to the flow chart of FIG. 17, in which an evoked event (e.g., a QRS complex) decreases a passband bandwidth and gain for a period of time.

DETAILED DESCRIPTION

Figure 1:
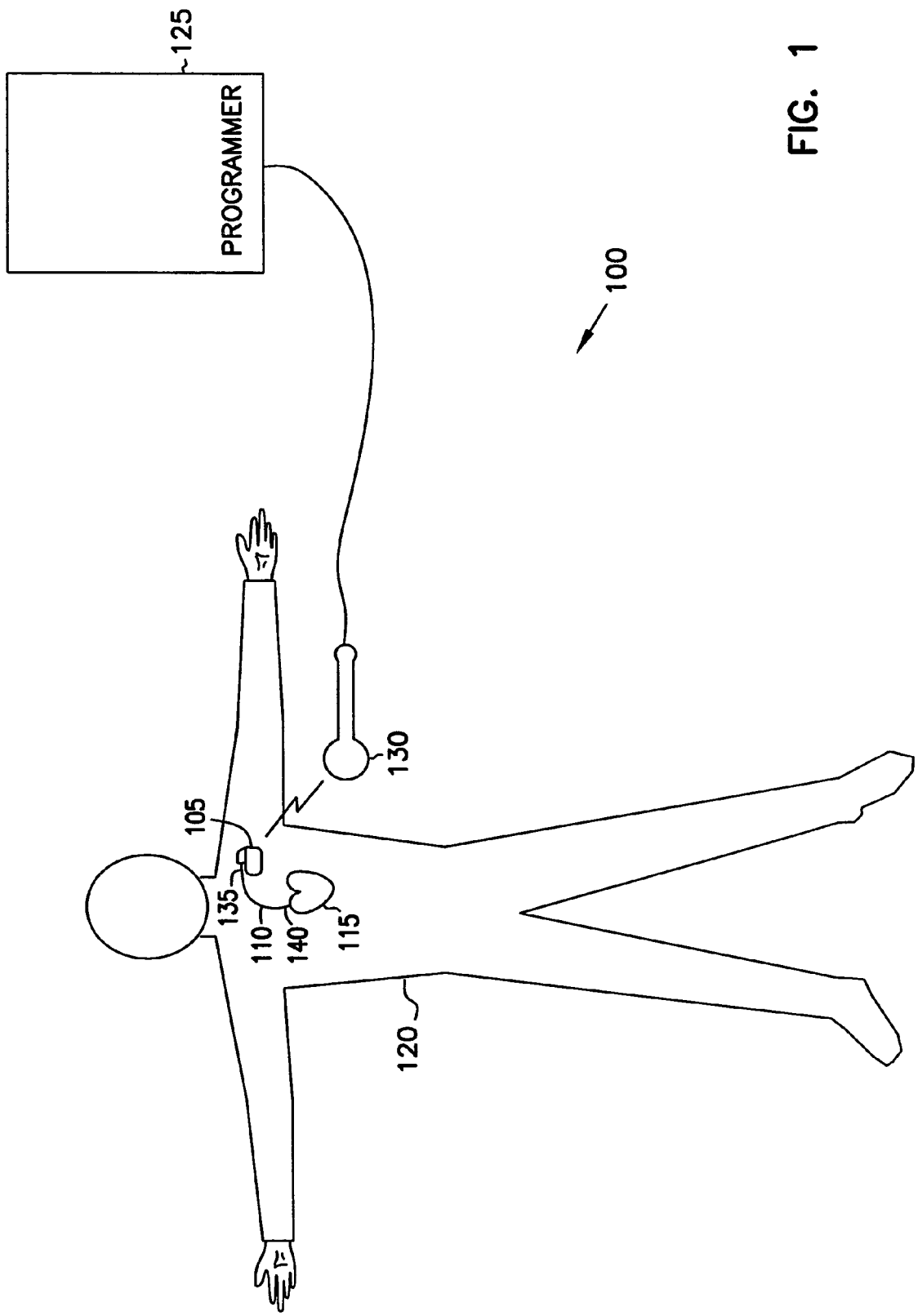
FIG. 1 is a schematic drawing illustrating one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

This document describes, among other things, a cardiac rhythm management system with a time-dependent frequency response for sensed heart signals. A change in the frequency response is triggered by a sensed or evoked event to make it less sensitive to the detection of a subsequent event for a period of time. This provides better discrimination between particular events included in a heart signal so that appropriate therapy can be delivered to the patient based such events.

FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110 to a heart 115 of patient 120. System 100 also includes an external programmer 125 providing wireless communication with device 105 using a telemetry device 130. Lead 110 includes a proximal end 135, which is coupled to device 105, and a distal end 140, which is coupled to one or more portions of heart 115.

Figure 2:
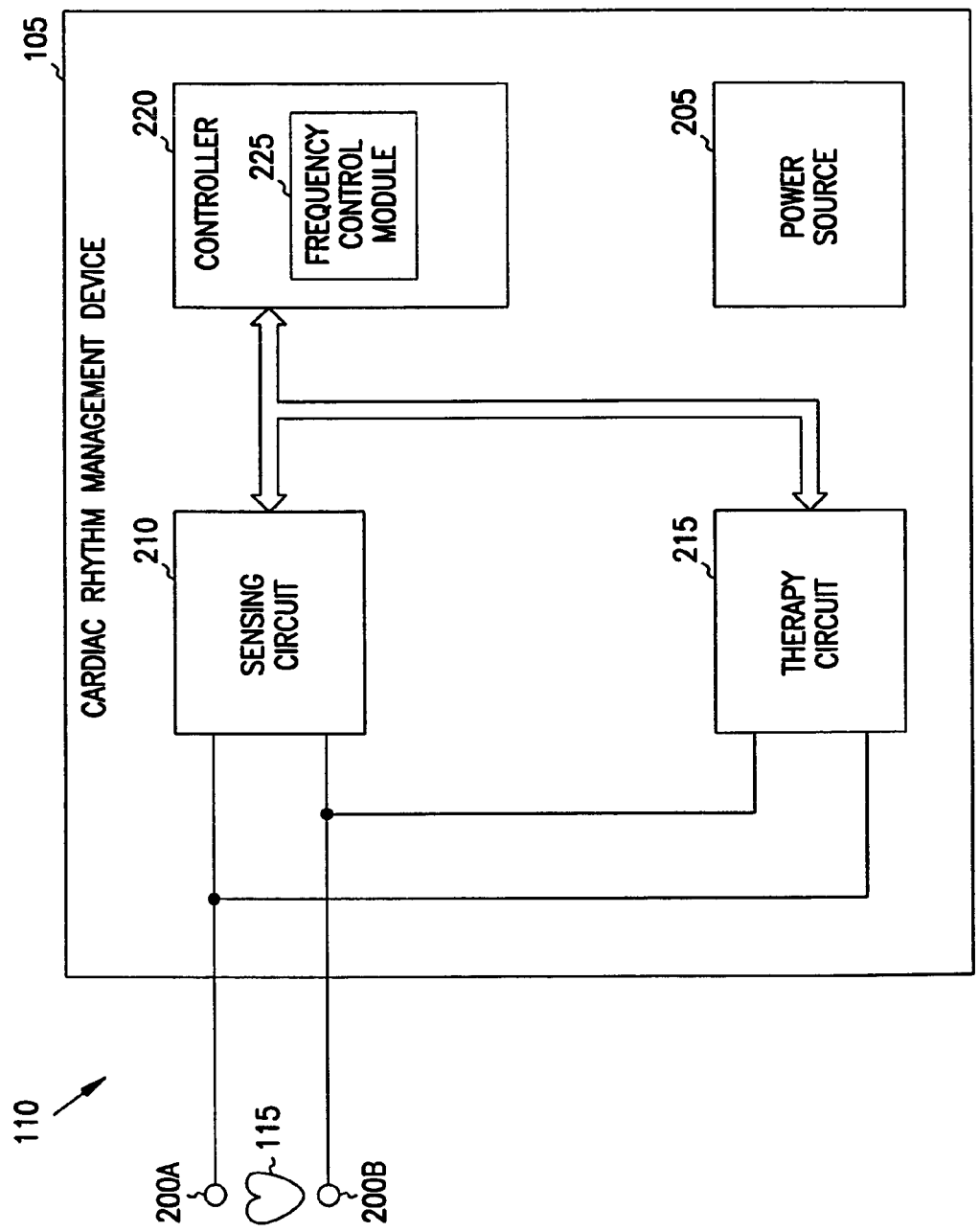
FIG. 2 is a schematic drawing illustrating one embodiment of portions of a cardiac rhythm management device and electrodes coupled to the heart, the device including a sensing circuit in which a frequency response is adjusted.

FIG. 2 is a schematic drawing illustrating, by way of example, but not by way of limitation, one embodiment of portions of cardiac rhythm management device 105, and electrodes 200A-B coupled to heart 115. In this embodiment device 105 includes a power source 205. A sensing circuit 210 senses intrinsic heart signals obtained at electrodes 200A-B or otherwise. A therapy circuit 215 is coupled to electrodes 200A-B, or to other electrodes coupled to heart 115, for delivering pacing stimulations and/or defibrillation countershock therapy. A microprocessor or other controller 220 receives signals from, and provides control signals to, sensing circuit 210 and therapy circuit 215.

Sensing circuit 210 includes continuous-time and/or discrete-time (e.g., switched capacitor) amplification and filter circuits, which provide an overall frequency response of sensing circuit 210. In one embodiment, controller 220 includes a frequency control module 225 for providing control signals for adjusting a frequency response of portions of sensing circuit 210, as discussed below. The frequency response is adjusted in response to a detected event obtained from the intrinsic heart signal and/or an evoked event obtained by providing therapy (e.g., a pacing stimulation) from therapy circuit 215.

Figure 3:
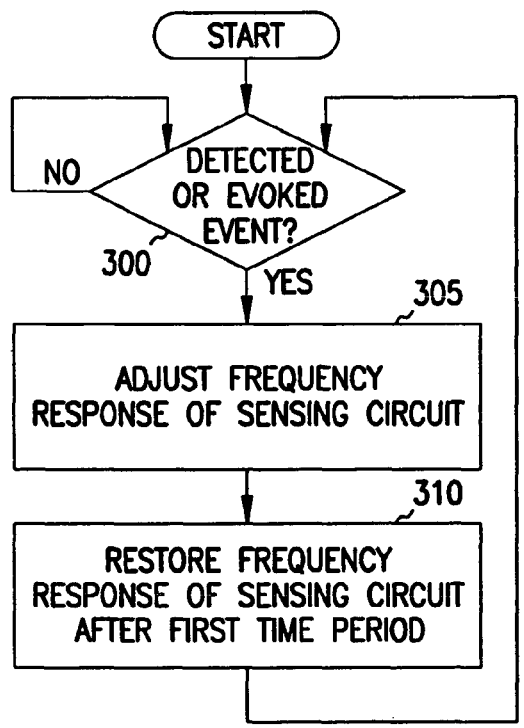
FIG. 3 is a flow chart illustrating one embodiment of operating a cardiac rhythm management device.

FIG. 3 is a flow chart illustrating generally, by way of example, but not by way of limitation, one embodiment of operating device 105. At step 300, if an intrinsic event on the heart signal is detected by sensing circuit 210, or if therapy circuit 215 delivers therapy to evoke an event on the heart signal, then at step 305, a frequency response of sensing circuit 210 is adjusted. At step 310, after a first time period the frequency response of sensing circuit 210 is then restored, to its value prior to step 305, until another detected or evoked event occurs at step 300.

Example with Highpass Pole

Figure 4:
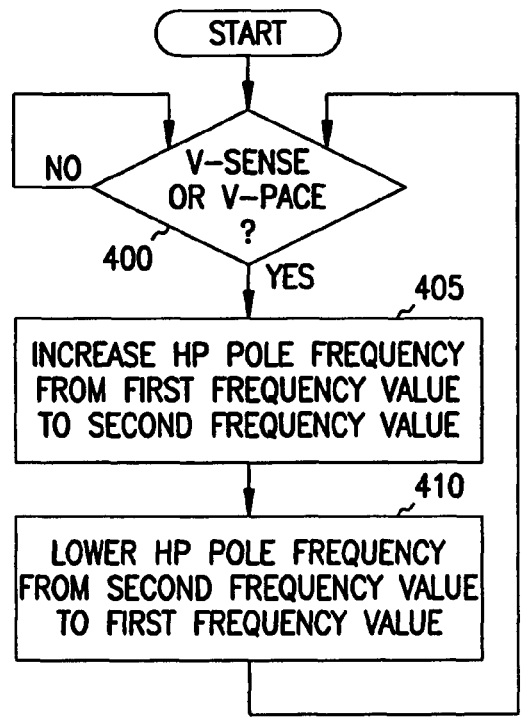
FIG. 4 is a flow chart illustrating another embodiment of operating a cardiac rhythm management device in which a sensed or evoked event (e.g., a ventricular sense or pace) triggers an increase in a highpass pole frequency for a period of time.
Figure 5:
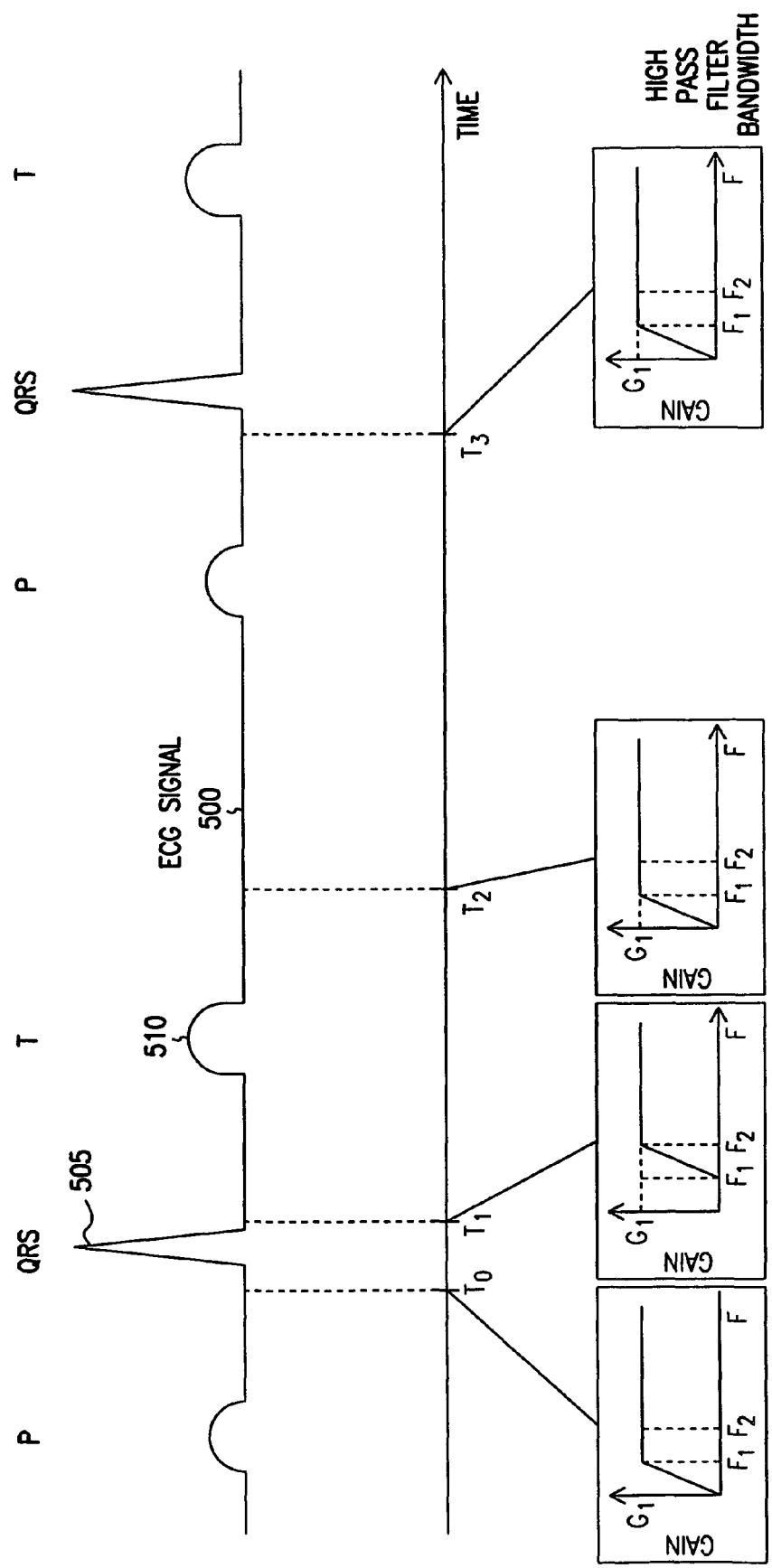
FIG. 5 is a signal flow graph, corresponding to the flow chart of FIG. 4, illustrating an intrinsic heart signal and frequency bandwidths of portions of the sensing circuit, in which a sensed event (e.g., a QRS complex) triggers an increase in a highpass pole frequency for a period of time.

FIG. 4 is a flow chart illustrating generally, by way of example, but not by way of limitation, another embodiment of operating device 105. FIG. 5 is a signal flow graph, corresponding to the flow chart of FIG. 4, illustrating intrinsic heart signal 500 and frequency bandwidths of portions of sensing circuit 210. At time t0, before step 400, sensing circuit 210 includes, among other things, a highpass frequency response that includes at least one highpass pole at or near a first frequency value, $f_1$.

At step 400 and time $t_1$, if an intrinsic ventricular event, such as QRS complex 505, is sensed or ventricular therapy, such as a ventricular pacing stimulation, is delivered, then at step 405, a highpass pole frequency increases from a first frequency value, $f_1$, to a higher second frequency value, $f_2$. As a result, sensing circuit 210 is subsequently more likely to reject lower frequency events such as T-wave 510, which includes frequency components below $f_2$. Thus, the attenuation of T-wave 510 and other low frequency events is increased immediately after QRS complex 505 is detected. Stated differently, sensing circuit 210 is less sensitive to T-wave detection during a time period immediately following a QRS detection. Sensing circuit is therefore less likely to erroneously detect a particular T-wave 510 as a QRS complex.

Figure 6:
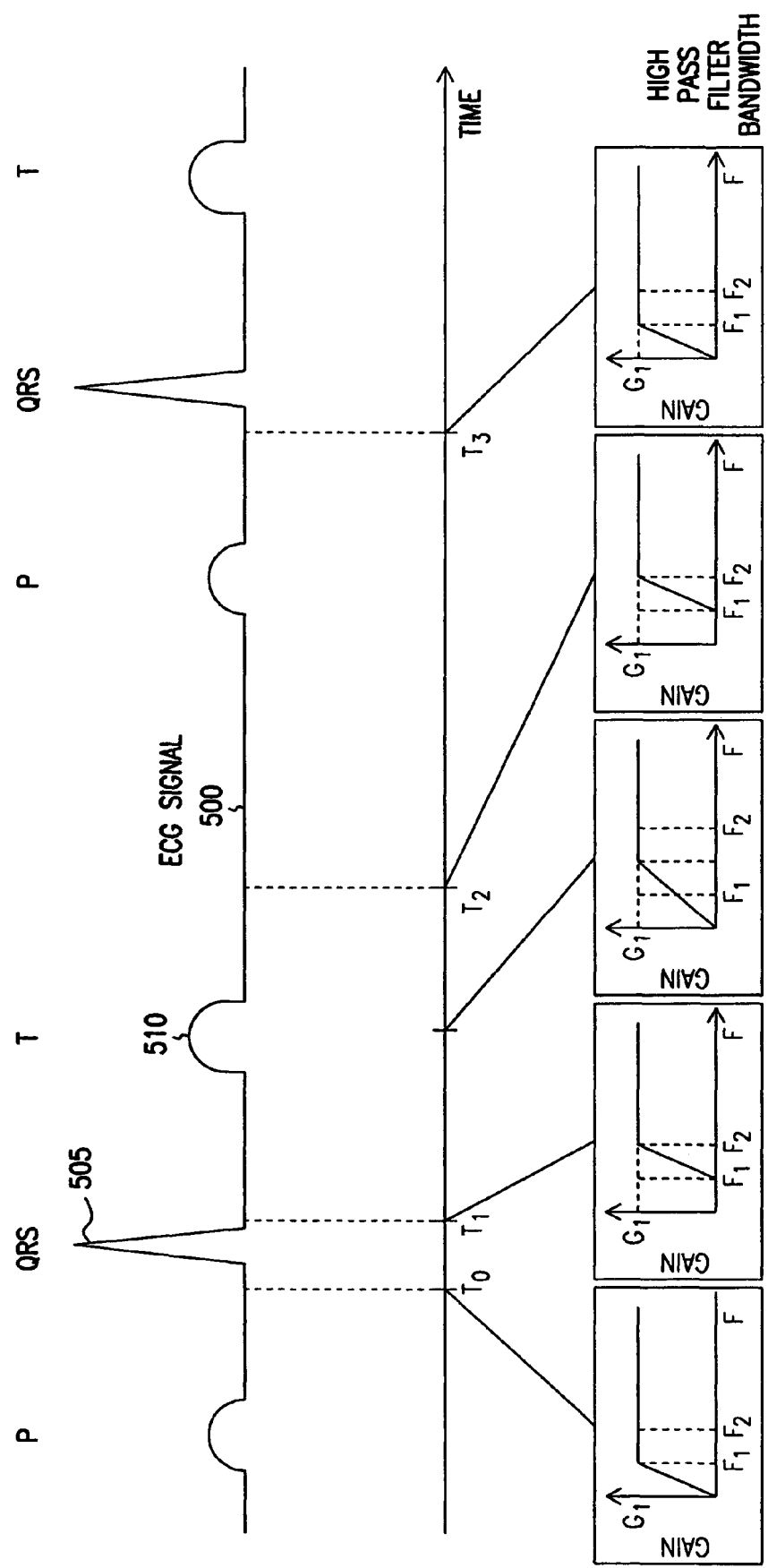
FIG. 6 is a signal flow graph, corresponding to the flow chart of FIG. 4, illustrating an intrinsic heart signal and frequency bandwidths of portions of the sensing circuit, in which an event (e.g., a QRS complex) triggers an increase in a highpass pole frequency, followed by a gradual decrease in the highpass pole frequency during a period of time.

At step 410 and time $t_2$, the highpass pole frequency of sensing circuit 210 decreases from $f_2$ back to $f_1$. As a result, after the first time period $t_2$-$t_1$, sensing circuit 210 is again made more sensitive to QRS complexes, which include frequency components above $f_1$. In one embodiment, the highpass pole frequency is switched from $f_1$ to $f_2$ at time $t_1$, and switched back to $f_1$ at time $t_2$. In another embodiment, the highpass pole frequency is switched from $f_1$ to $f_2$ at time $t_1$, but the highpass pole frequency is gradually decreased from $f_2$ back toward $f_1$ during the first time period $t_2$-$t_1$, such that the highpass pole frequency approaches $f_1$ at time $t_2$, as illustrated in FIG. 6. In this embodiment, the frequency response is time dependent during the first time period $t_2$-$t_1$. In one embodiment, the first time period $t_2$-$t_1$ is greater than or equal to 250 milliseconds, such as approximately between 250 milliseconds and 500 milliseconds or at approximately 500 milliseconds. Thus, the first time period, in this embodiment, is sufficiently long to allow the ventricle to repolarize (allow a T-wave) while the sensitivity of the sensing circuit 210 is still reduced. In one embodiment, programmer 125 communicates to device 105 a parameter controlling one of: (a) the frequency response of the sensing circuit, and (b) the duration of the first time period.

Figure 7:
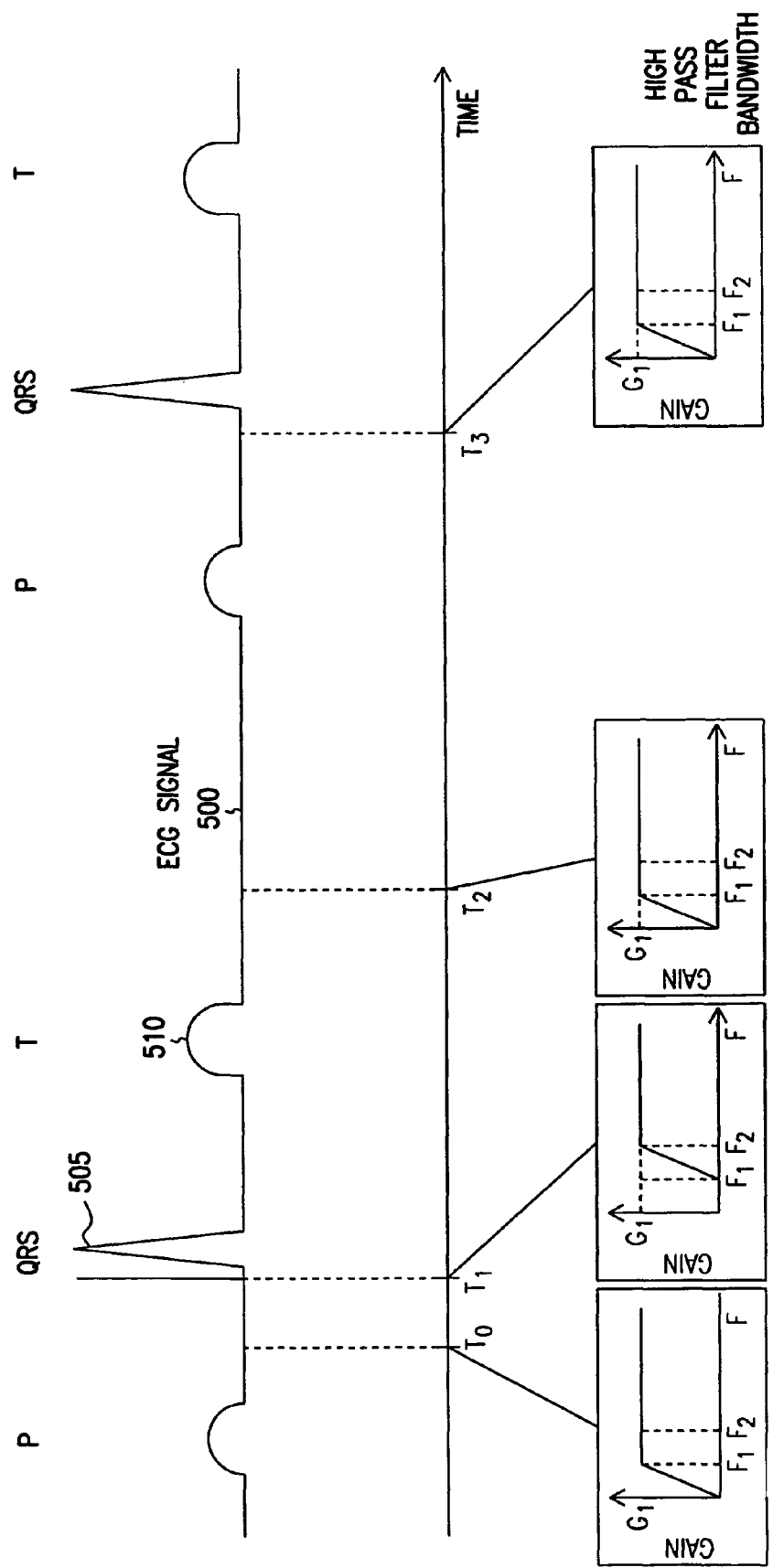
FIG. 7 is a signal flow graph, corresponding to the flow chart of FIG. 4, in which an evoked event (e.g., a QRS complex) triggers an increase in the highpass pole frequency for a period of time.

FIG. 7 is a signal flow graph, similar to FIG. 5, illustrating the case of step 400 in which therapy, such as a ventricular pacing stimulation, is delivered at time $t_1$, thereby evoking QRS complex 505, and initiating the adjustment in the frequency response of sensing circuit 210 by increasing the highpass pole from $f_1$ to $f_2$ for a first time period $t_2$-$t_1$ to make the sensing circuit less sensitive to T-wave 510 during the first time period.

Example with Lowpass Pole

Figure 8:
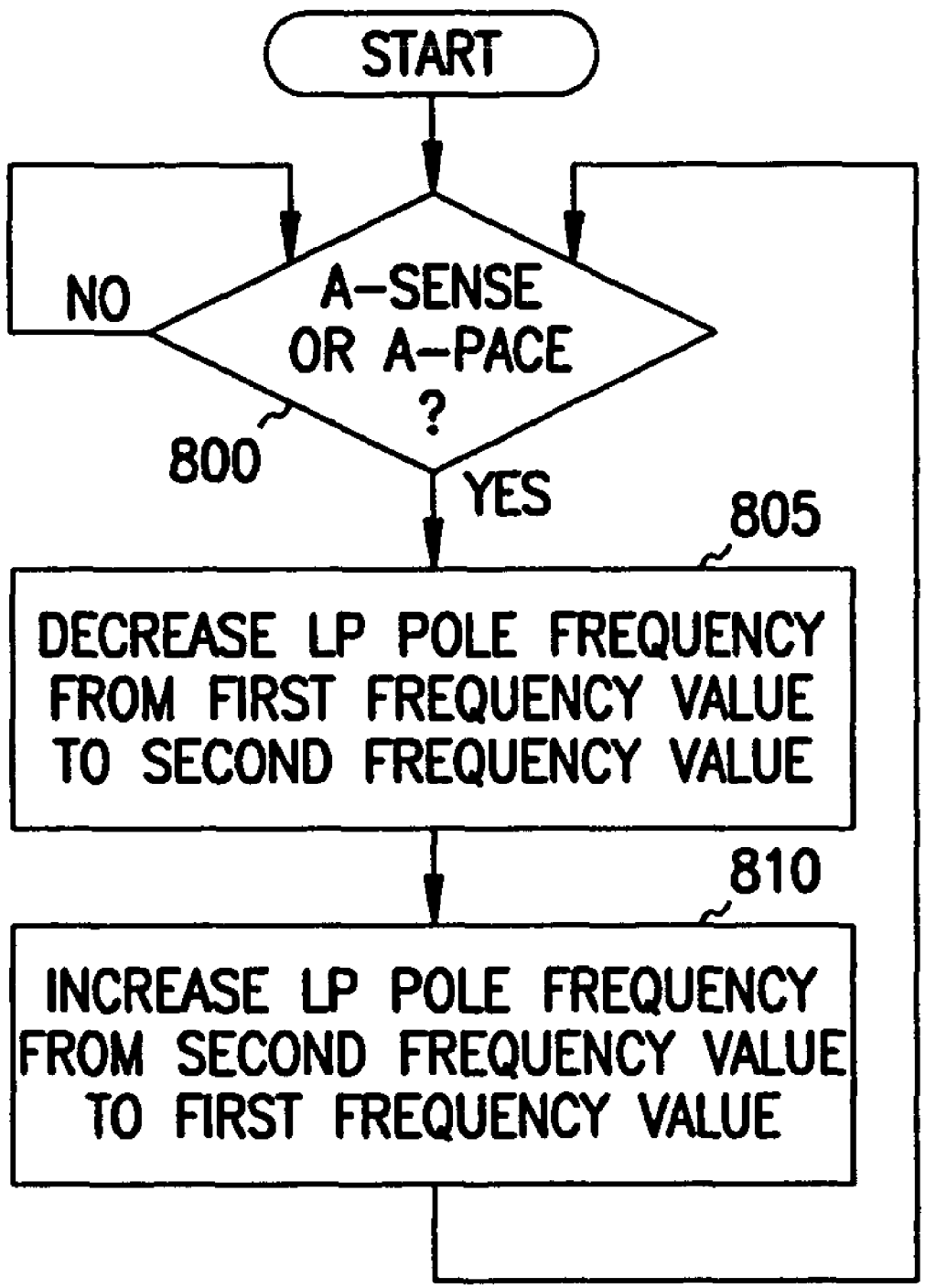
FIG. 8 is a flow chart illustrating another embodiment of operating a cardiac rhythm management device in which a sensed or evoked event (e.g., an atrial sense of pace) triggers a decrease in a lowpass pole frequency for a period of time.
Figure 9:
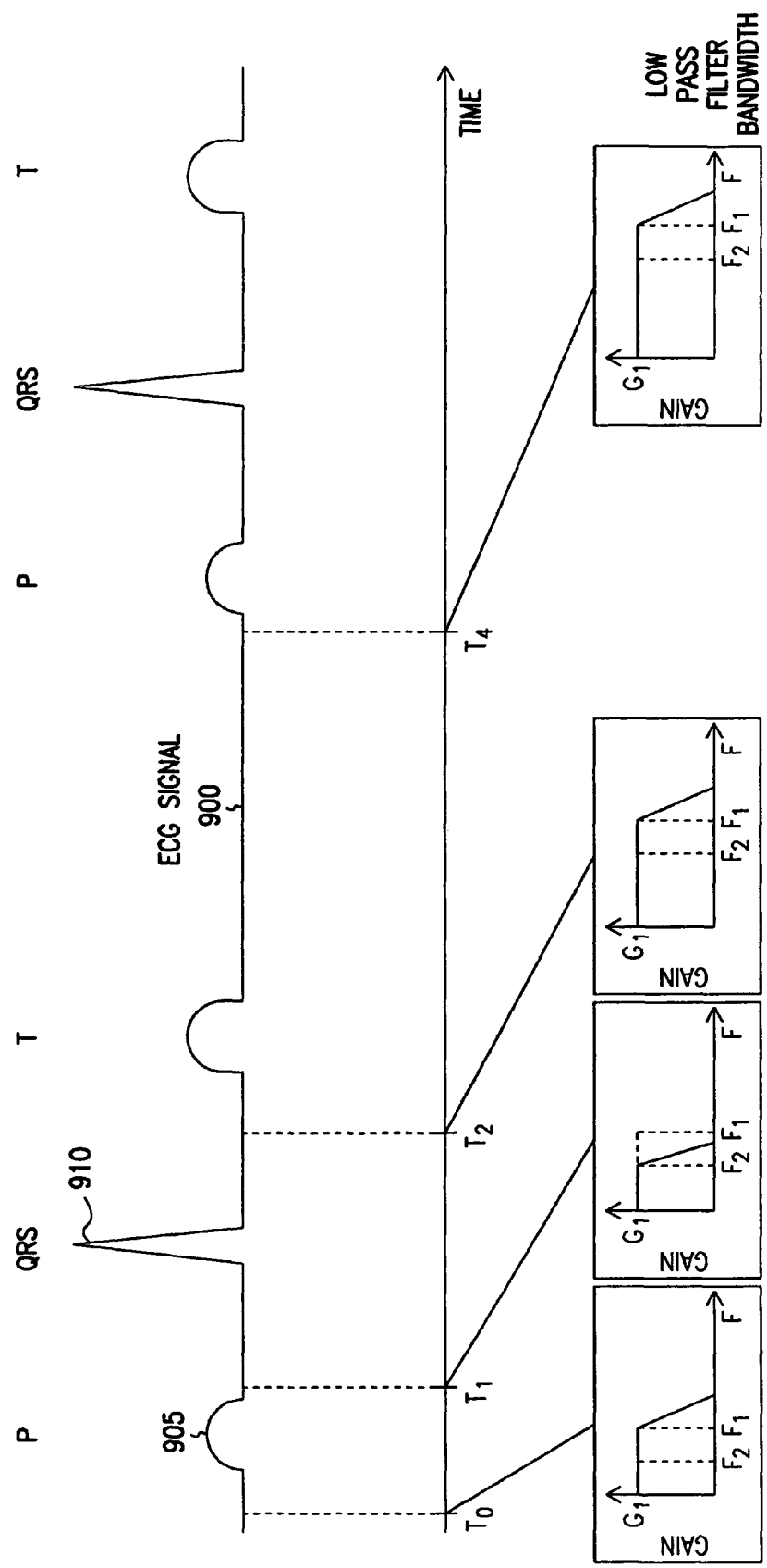
FIG. 9 is a signal flow graph, corresponding to the flow chart of FIG. 8, illustrating an intrinsic heart signal and frequency bandwidths of portions of the sensing circuit, in which a sensed event (e.g., a P-wave) triggers a decrease in a lowpass pole frequency for a period of time.

FIG. 8 is a flow chart illustrating generally, by way of example, but not by way of limitation, another embodiment of operating device 105. FIG. 9 is a signal flow graph, corresponding to the flow chart of FIG. 8, illustrating intrinsic heart signal 900 and frequency bandwidths of portions of sensing circuit 210. At time $t_0$, before step 800, sensing circuit 210 includes, among other things, a lowpass frequency response that includes at least one lowpass pole at or near a first frequency value, $f_1$.

At step 800 and time $t_1$, if an intrinsic atrial event, such as P-wave 905, is sensed or atrial therapy, such as an atrial pacing stimulation, is delivered, then at step 805, the lowpass pole frequency decreases from first frequency value, $f_1$, to a lower second frequency value, $f_2$. As a result, sensing circuit 210 is subsequently more likely to reject higher frequency events such as QRS complex 910, which includes frequency components above $f_2$. Thus, the attenuation of QRS complex 910 and other high frequency events is increased immediately after P-wave 905 is detected. Stated differently, sensing circuit 210 is less sensitive to QRS complex detection during a time period immediately following a P-wave detection. Sensing circuit is therefore less likely to erroneously detect a particular QRS complex 910 as a P-wave.

Figure 10:
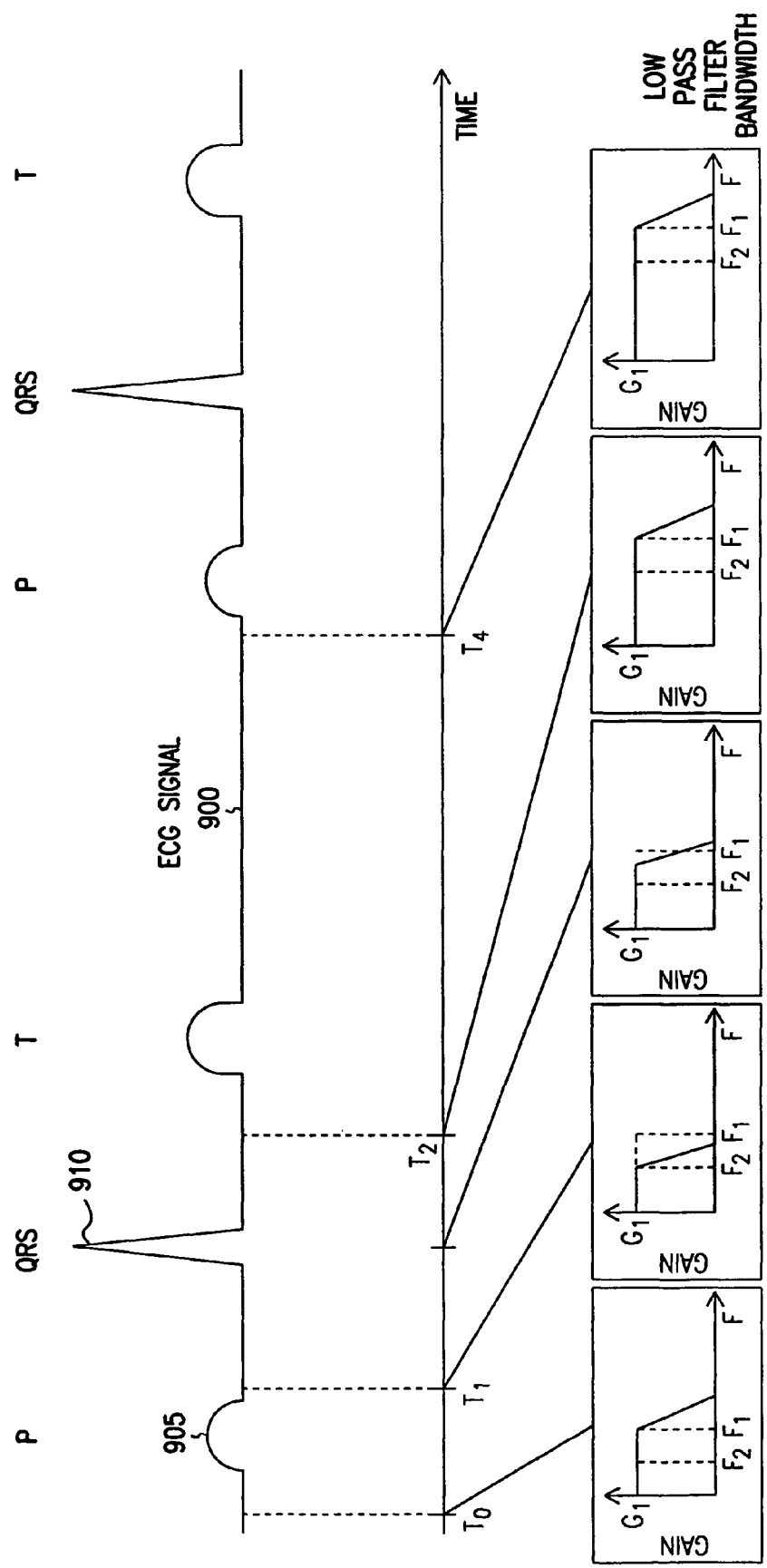
FIG. 10 is a signal flow graph, corresponding to the flow chart of FIG. 8, illustrating an intrinsic heart signal and frequency bandwidths of portions of the sensing circuit in which an event (e.g., a P-wave) triggers a decrease in a lowpass pole frequency, followed by a gradual increase in the lowpass pole frequency during a period of time.

At step 810 and time $t_2$, the lowpass pole frequency of sensing circuit 210 increases from $f_2$ to $f_1$. As a result, after the first time period $t_2$-$t_1$, sensing circuit 210 is more sensitive to P-waves, which include frequency components below $f_1$. In one embodiment, the lowpass pole frequency is switched from $f_1$ to $f_2$ at time $t_1$, and switched back to $f_1$ at time $t_2$. In another embodiment, the lowpass pole frequency is switched from $f_1$ to $f_2$ at time $t_1$, but the lowpass pole frequency is gradually increased from $f_2$ back toward $f_1$ during the first time period $t_2$-$t_1$, such that the lowpass pole frequency approaches $f_1$ at time $t_2$, as illustrated in FIG. 10. In this embodiment, the frequency response is time dependent during the time period $t_2$-$t_1$.

Figure 11:
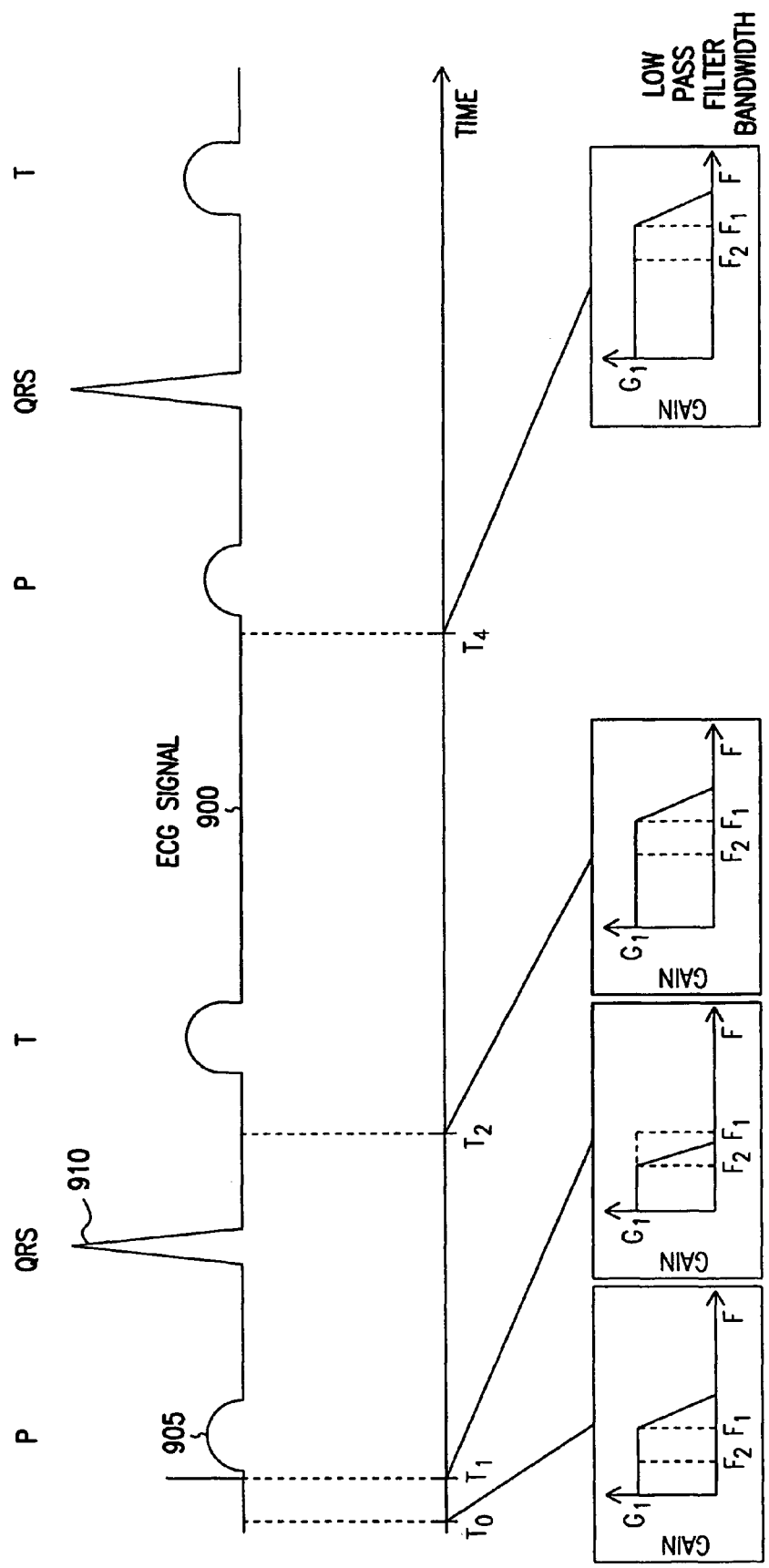
FIG. 11 is a signal flow graph, corresponding to the flow chart of FIG. 8, in which an evoked event (e.g., a P-wave) triggers a decrease in the lowpass frequency.

FIG. 11 is a signal flow graph, similar to FIG. 9, illustrating the case of step 800 in which therapy, such as an atrial pacing stimulation, is delivered at time $t_1$, thereby evoking P-wave 905, and initiating the adjustment in the frequency response of sensing circuit 210 by decreasing the lowpass pole from $f_1$ to $f_2$ for a first time period $t_2$-$t_1$, to make the sensing circuit less sensitive to QRS complex 910 during the first time period.

Example with Lowpass and Highpass Poles

Figure 12:
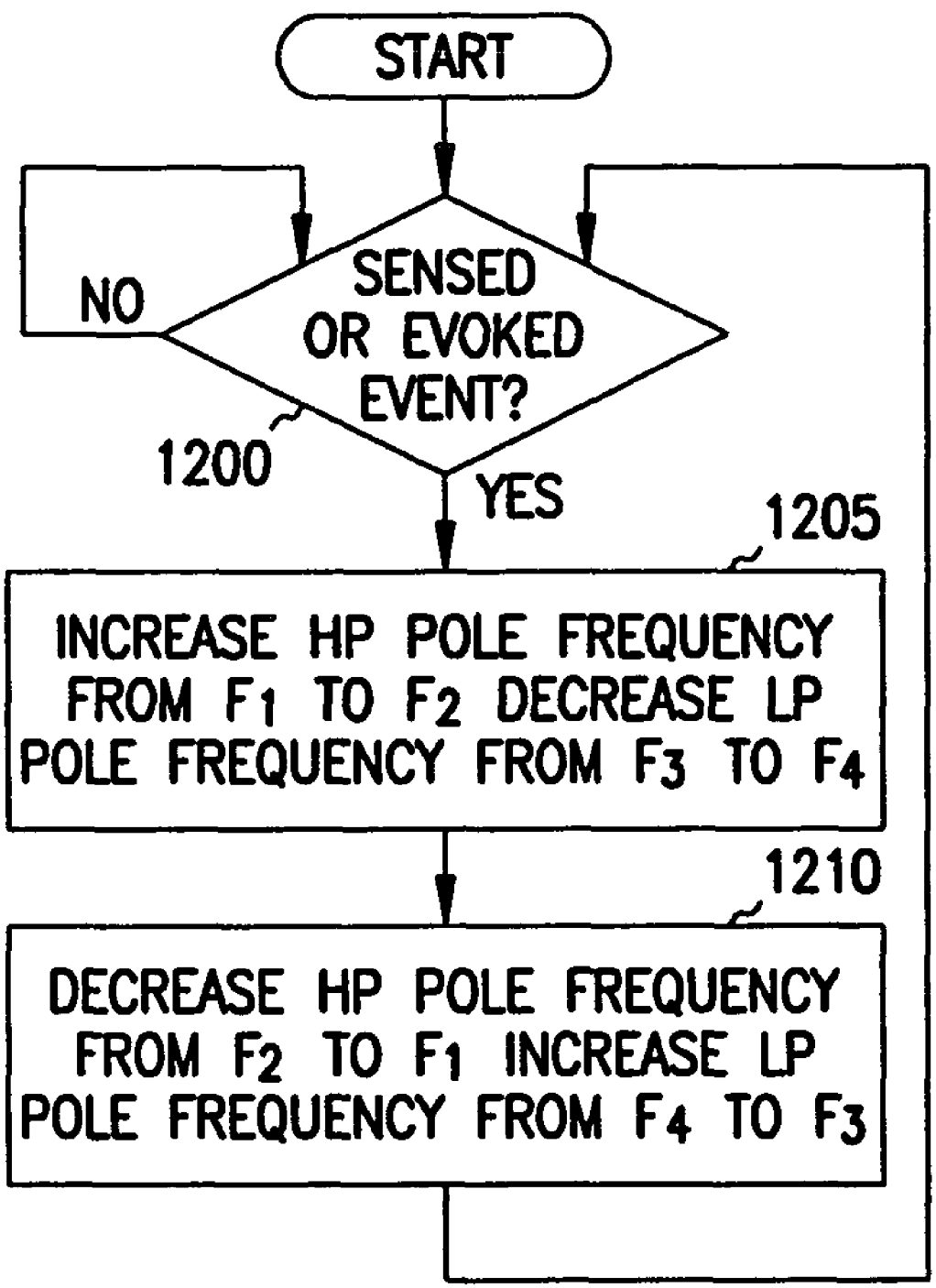
FIG. 12 is a flow chart illustrating another embodiment of operating a cardiac rhythm management device in which a sensed or evoked event (e.g., a QRS complex) triggers a narrowing of a passband bandwidth for a period of time.
Figure 13:
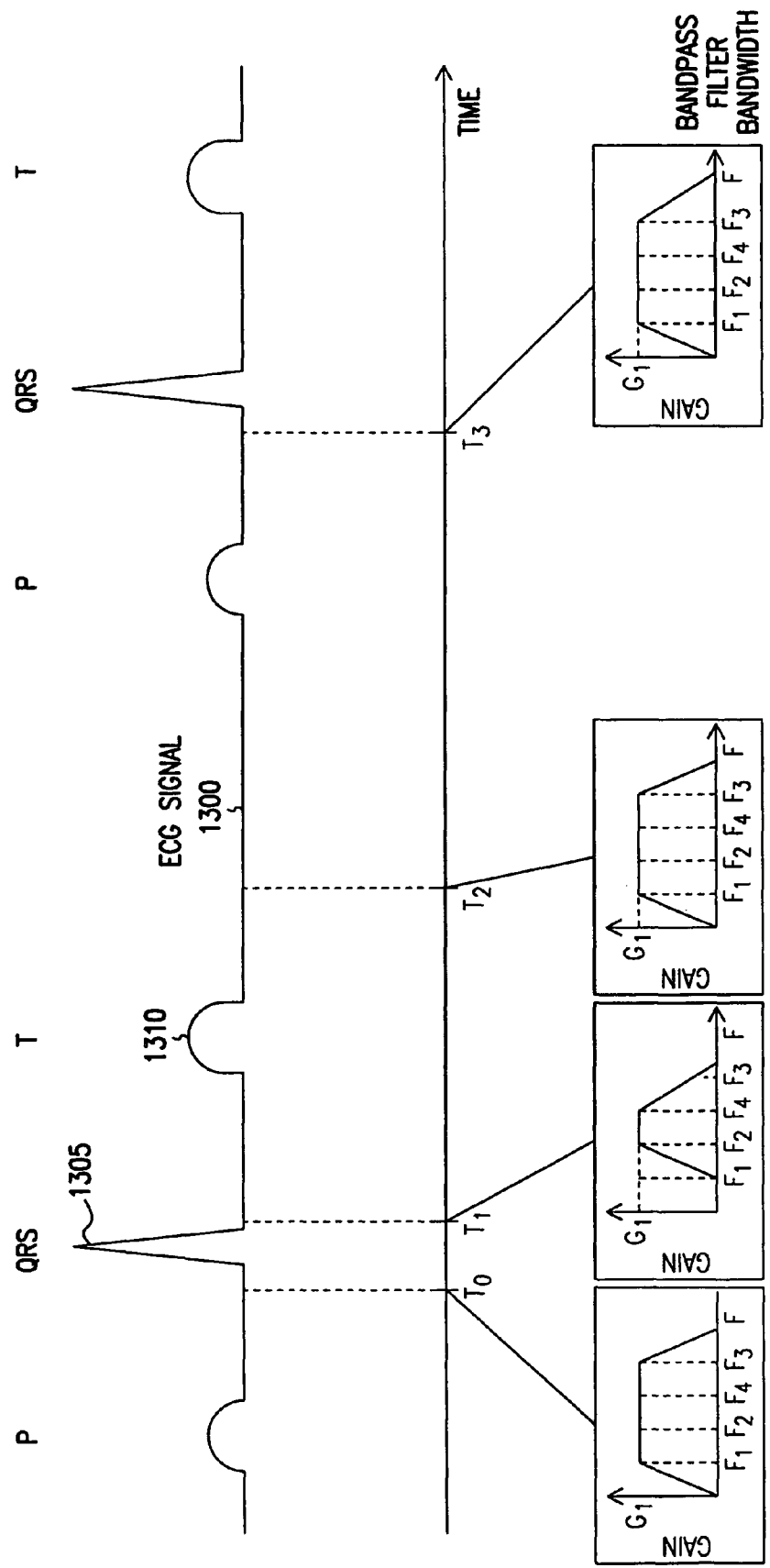
FIG. 13 is a signal flow graph, corresponding to the flow chart of FIG. 12, illustrating an intrinsic heart signal and frequency bandwidths of portions of the sensing circuit, in which a sensed event (e.g., a QRS complex) narrows a passband bandwidth for a period of time.

FIG. 12 is a flow chart illustrating generally, by way of example, but not by way of limitation, another embodiment of operating device 105. FIG. 13 is a signal flow graph of intrinsic heart signal 1300 and frequency bandwidths of portions of sensing circuit 210, corresponding to FIG. 12. At time to, before step 800, sensing circuit 210 includes, among other things, a bandpass frequency response that includes at least one highpass pole at or near a first frequency value, $f_1$, and at least one lowpass pole at or near a third frequency value, $f_3$.

At step 800 and time $t_1$, if an intrisic sensed event, such as QRS complex 1305, is sensed or therapy, such as a pacing stimulation, is delivered, then at step 1205, the highpass pole frequency increases from first frequency value, $f_1$, to a higher second frequency value, $f_2$, and the lowpass pole frequency decreases from third frequency value $f_3$ to a lower fourth frequency value $f_4$. As a result, sensing circuit 210 is subsequently more likely to reject frequencies outside the frequency range $f_4$-$f_2$, which includes frequencies of QRS complex 1305. Thus, attenuation and rejection of T-wave 1310 is increased immediately after QRS complex 1305 is detected. Stated differently, sensing circuit 210 is less sensitive to T-wave detection during a time period immediately following a QRS complex detection. Sensing circuit 210 is therefore less likely to erroneously detect a particular T-wave 1310 as a QRS complex.

Figure 14:
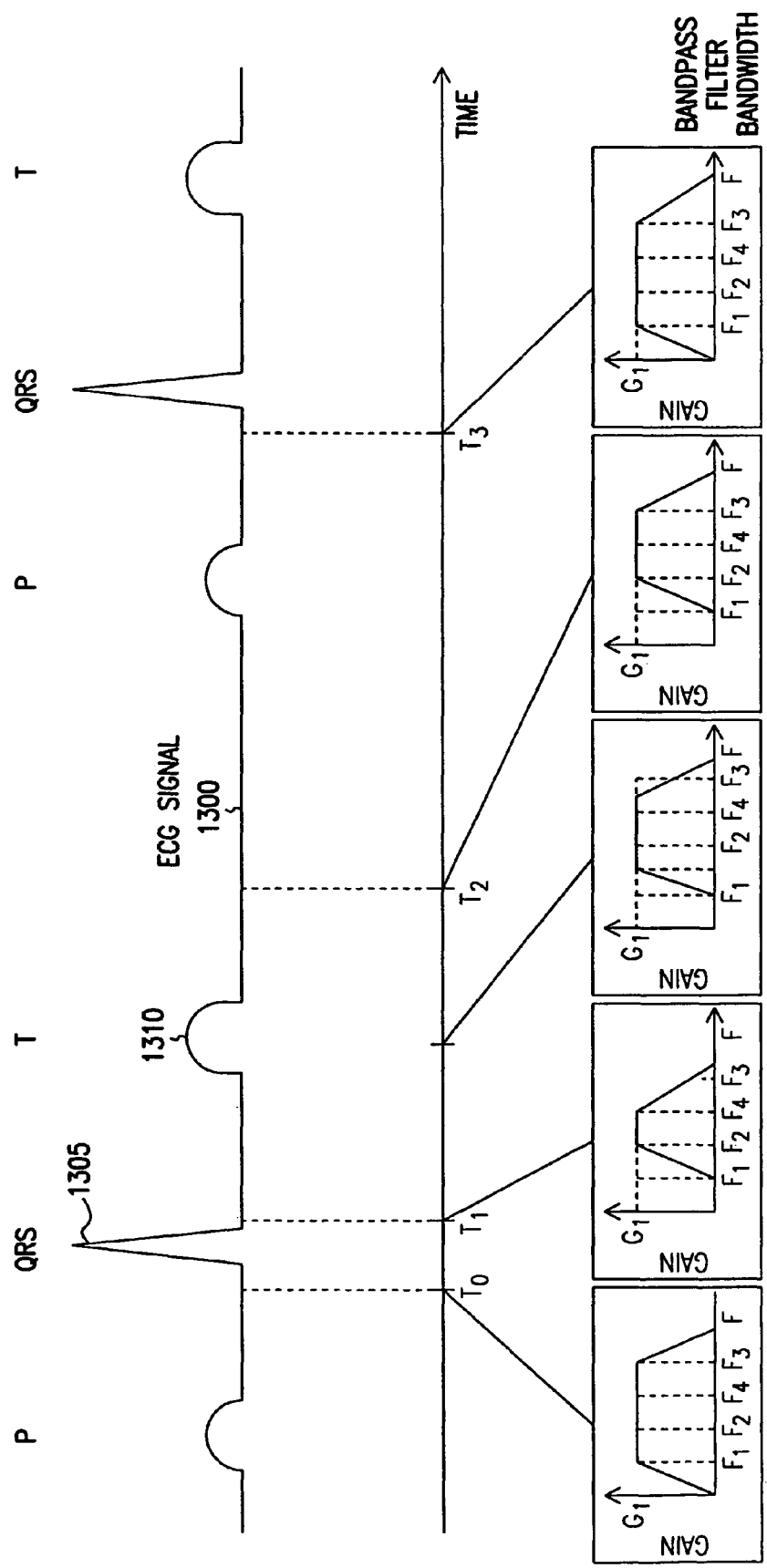
FIG. 14 is a signal flow graph, corresponding to the flow chart of FIG. 12, illustrating an intrinsic heart signal and frequency bandwidths of portions of the sensing circuit in which an event (e.g., a QRS complex) triggers a narrowing of a passband, followed by a gradual increase in the passband during a period of time.

At step 1210 and time $t_2$, the highpass pole frequency of sensing circuit 210 decreases from $f_2$ back to $f_1$, and the lowpass pole frequency of sensing circuit 210 increases from $f_4$ back to $f_3$. As a result, after the first time period $t_2$-$t_1$, such as during the time period $t_3$-$t_2$, sensing circuit 210 is made again more sensitive to T-waves. In one embodiment, the lowpass and highpass pole frequency are switched at time $t_1$ and switched back at time $t_2$. In another embodiment, the lowpass and highpass pole frequencies are switched at time $t_1$, and then gradually returned toward their original values during the first time period $t_2$-$t_1$, as illustrated in FIG. 14. In this embodiment, the frequency response is time dependent during the time period $t_2$-$t_1$.

Figure 15:
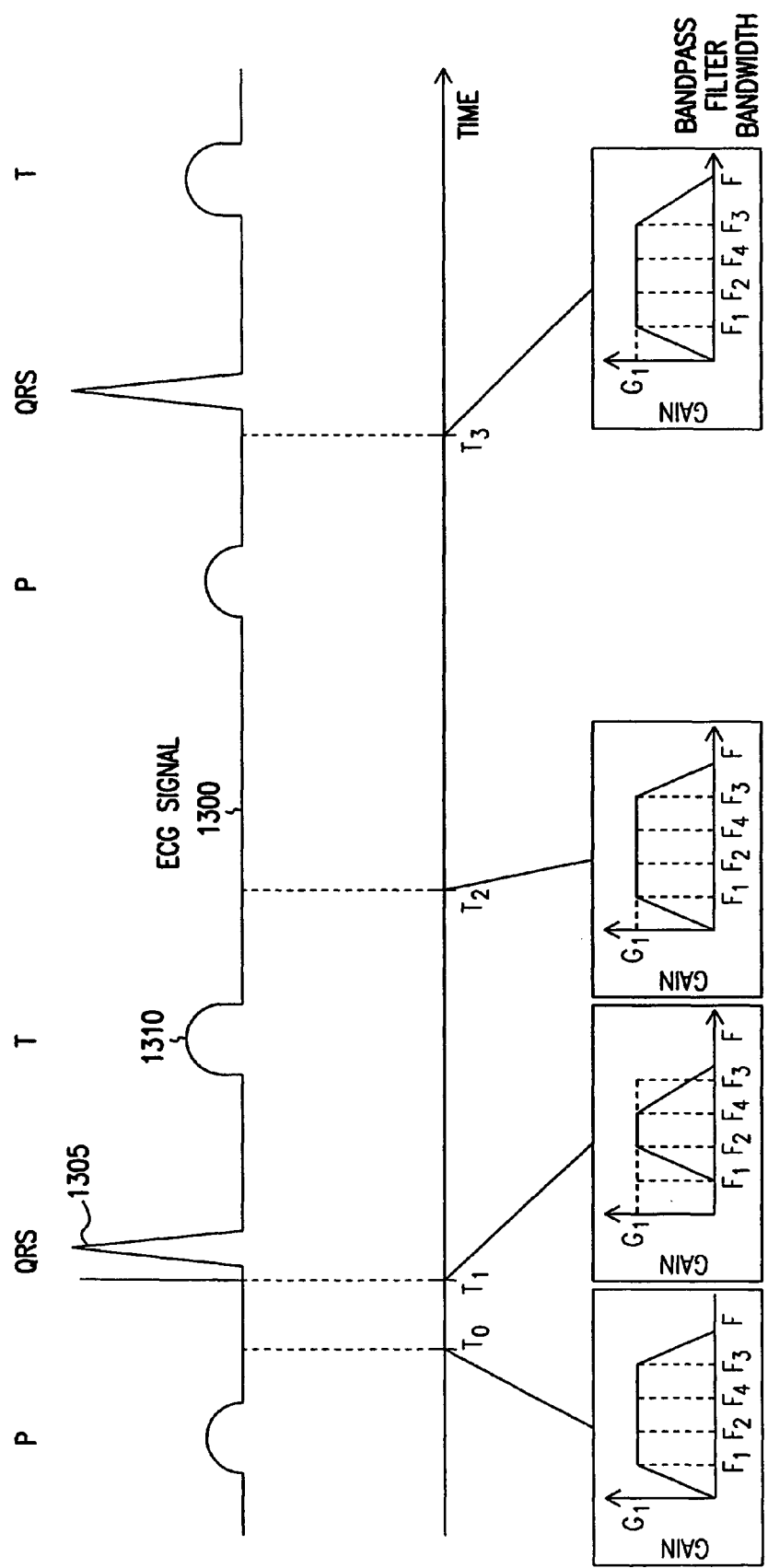
FIG. 15 is a signal flow graph, corresponding to the flow chart of FIG. 12, in which an evoked event (e.g., a QRS complex) narrows a passband bandwidth for a period of time.

FIG. 15 is a signal flow graph, similar to FIG. 13, illustrating the case of step 1200 in which therapy, such as a pacing stimulation, is delivered at time $t_1$, thereby evoking QRS complex 1305, and initiating the adjustment in the frequency response of sensing circuit 210 to make the sensing circuit less sensitive to T-wave 1310 during the first time period $t_2$-$t_1$.

Example with Frequency and Gain Adjustment

Figure 16:
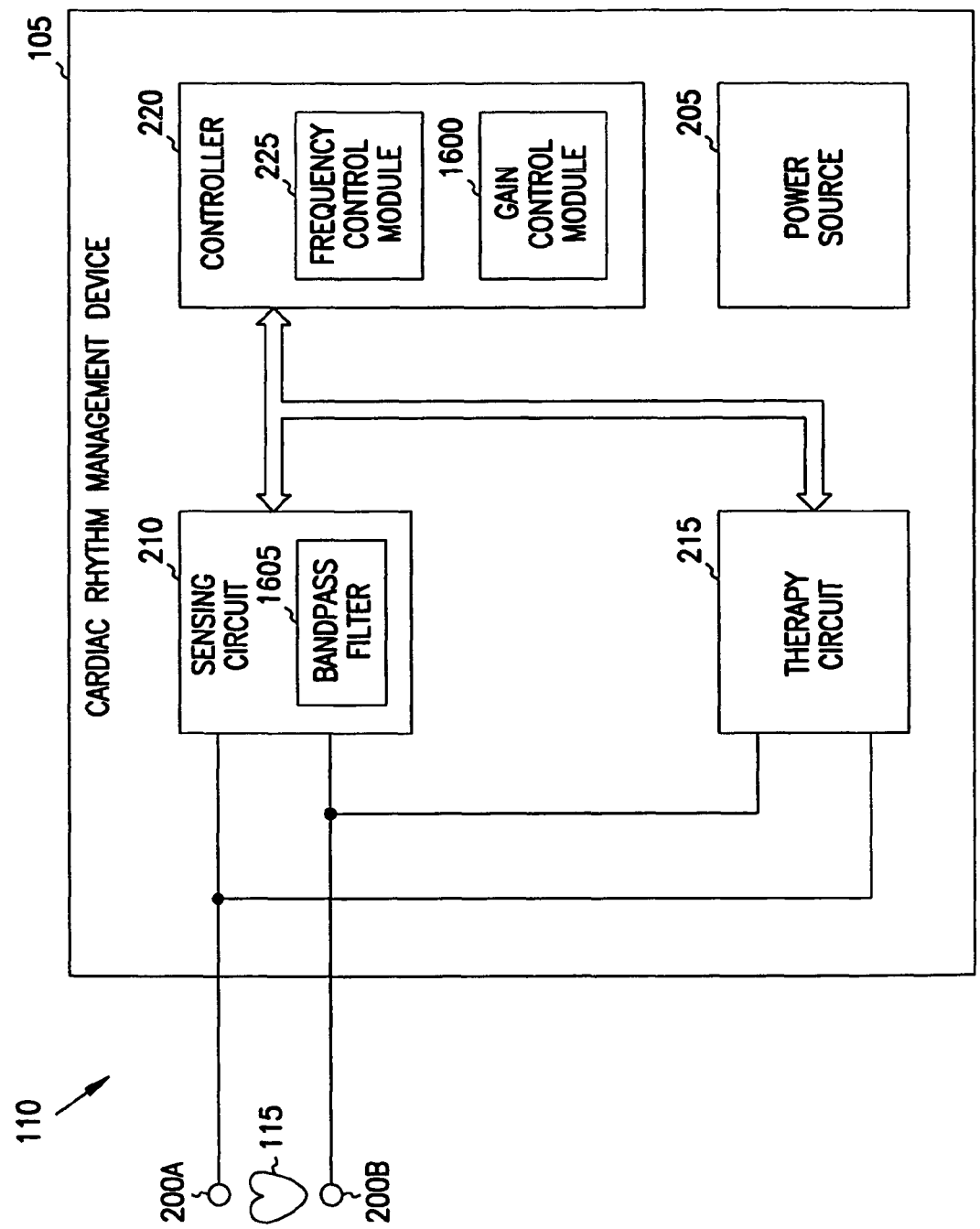
FIG. 16 is a schematic diagram illustrating one embodiment of portions of a cardiac rhythm management device and electrodes coupled to the heart, the device including a sensing circuit in which a gain and a bandwidth of a frequency response is adjusted.

FIG. 16 is a schematic diagram illustrating generally, by way of example, but not by way of limitation, another embodiment of device 105 in which controller 220 further includes a gain control module 1600, which provides control signals to a bandpass filter 1605 in sensing circuit 210 for controlling at least one passband gain contributing to the overall frequency response of sensing circuit 210, in addition to the frequency control module 225 that controls at least one frequency bandwidth of bandpass filter 1605 in sensing circuit 210.

Figure 17:
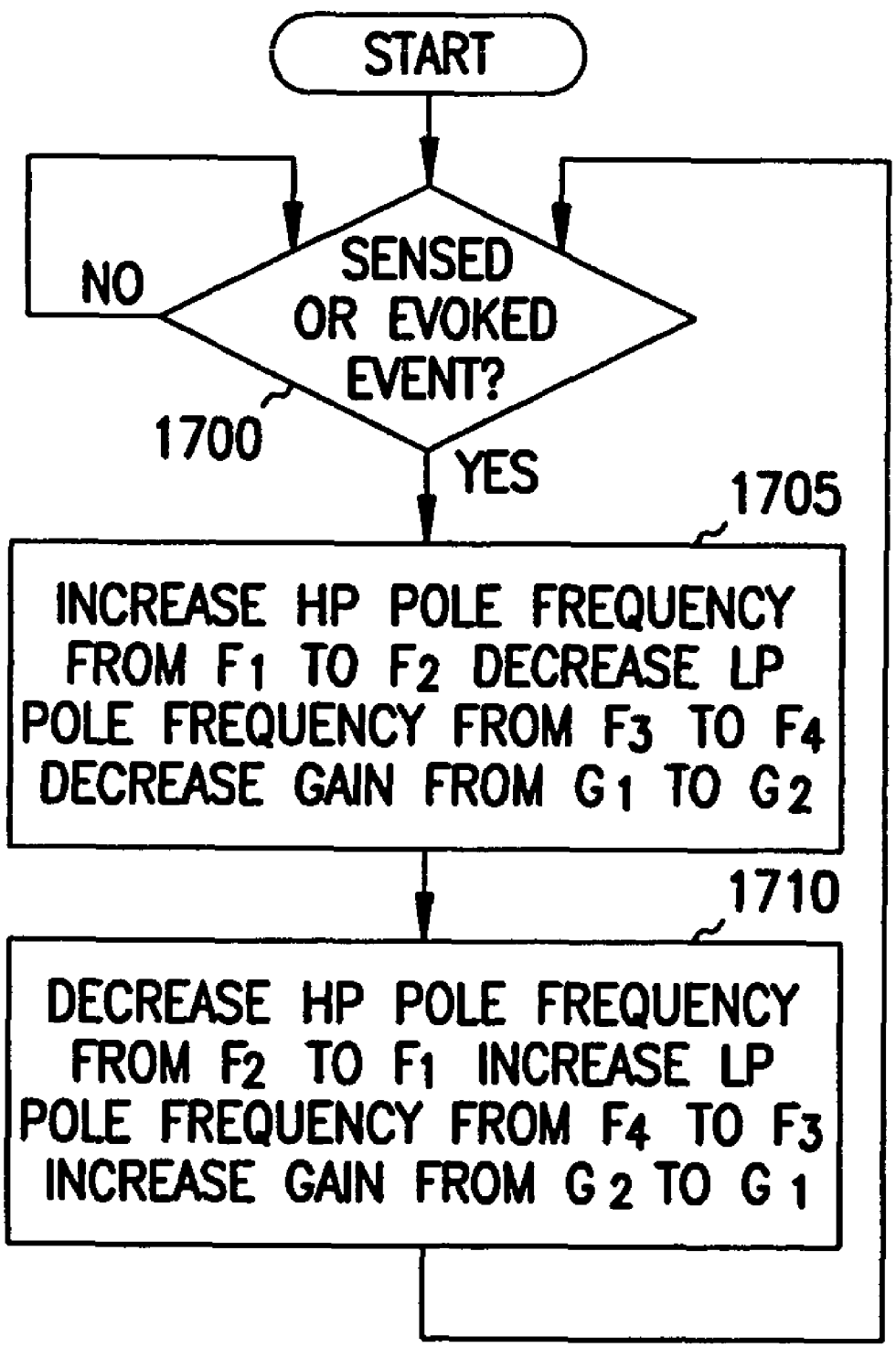
FIG. 17 is a flow chart illustrating another embodiment of operating a cardiac rhythm management device in which a sensed or evoked event (e.g., a QRS complex) triggers a narrowing of a passband bandwidth and a decrease in gain for a period of time.
Figure 18:
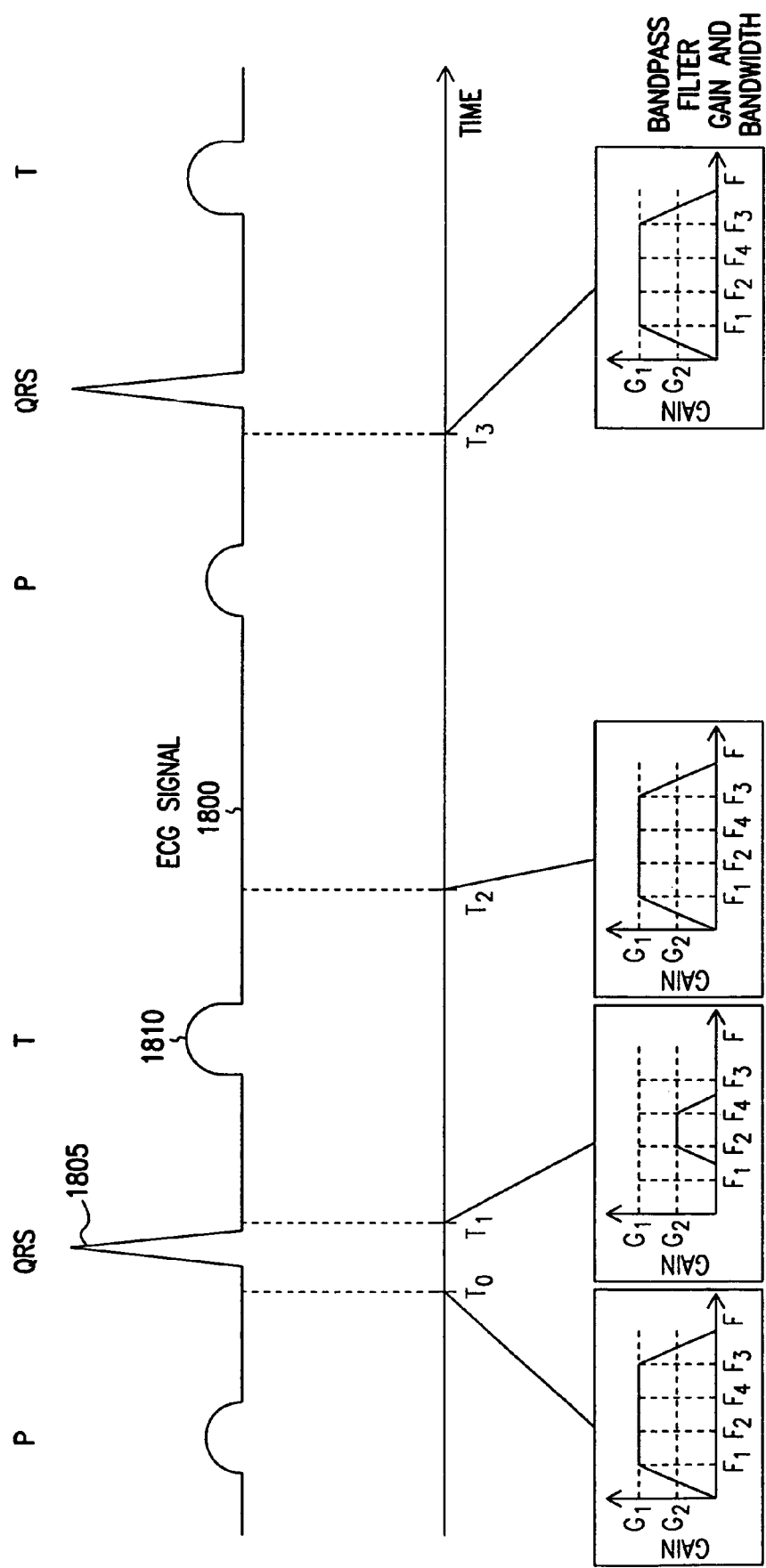
FIG. 18 is a signal flow diagram, corresponding to the flow chart of FIG. 17, illustrating an intrinsic heart signal and frequency response of portions of the sensing circuit, in which a sensed event (e.g., a QRS complex) decreases a passband bandwidth and gain for a period of time.

FIG. 17 is a flow chart illustrating generally, by way of example, but not by way of limitation, another embodiment of operating device 105 in which both the frequency bandwidth and gain are adjusted in response to a detected event obtained from the intrinsic heart signal and/or an evoked event obtained by providing therapy (e.g., a pacing stimulation) from therapy circuit 215. FIG. 18 is a signal flow graph, corresponding to the flow chart of FIG. 17, that illustrates intrinsic heart signal 1800 and frequency bandwidths of portions of sensing circuit 210. At time $t_0$, before step 1700, sensing circuit 210 includes, among other things, a bandpass frequency response that includes at least one highpass pole at or near a first frequency value, $f_1$, and at least one lowpass pole at or near a third frequency value, $f_3$, and a first passband gain of approximately $G_1$.

At step 1700 and time $t_1$, if an intrisic sensed event, such as QRS complex 1805, is sensed or therapy, such as a pacing stimulation, is delivered, then at step 1705, the highpass pole frequency increases from first frequency value, $f_1$, to a higher second frequency value, $f_2$, the lowpass pole frequency decreases from third frequency value $f_3$ to a lower fourth frequency value $f_4$, and the passband gain decreases from $G_1$ to a second passband gain of approximately $G_2$. As a result, sensing circuit 210 is subsequently less sensitive. Thus, attenuation and rejection of T-wave 1810, having frequency components that are very close in frequency to frequency components of QRS complex 1805, is increased immediately after QRS complex 1805 is detected. Stated differently, sensing circuit 210 is less sensitive to T-wave detection during a time period immediately following a QRS complex detection. Sensing circuit 210 is therefore less likely to erroneously detect a particular T-wave 1810 as a QRS complex.

Figure 19:
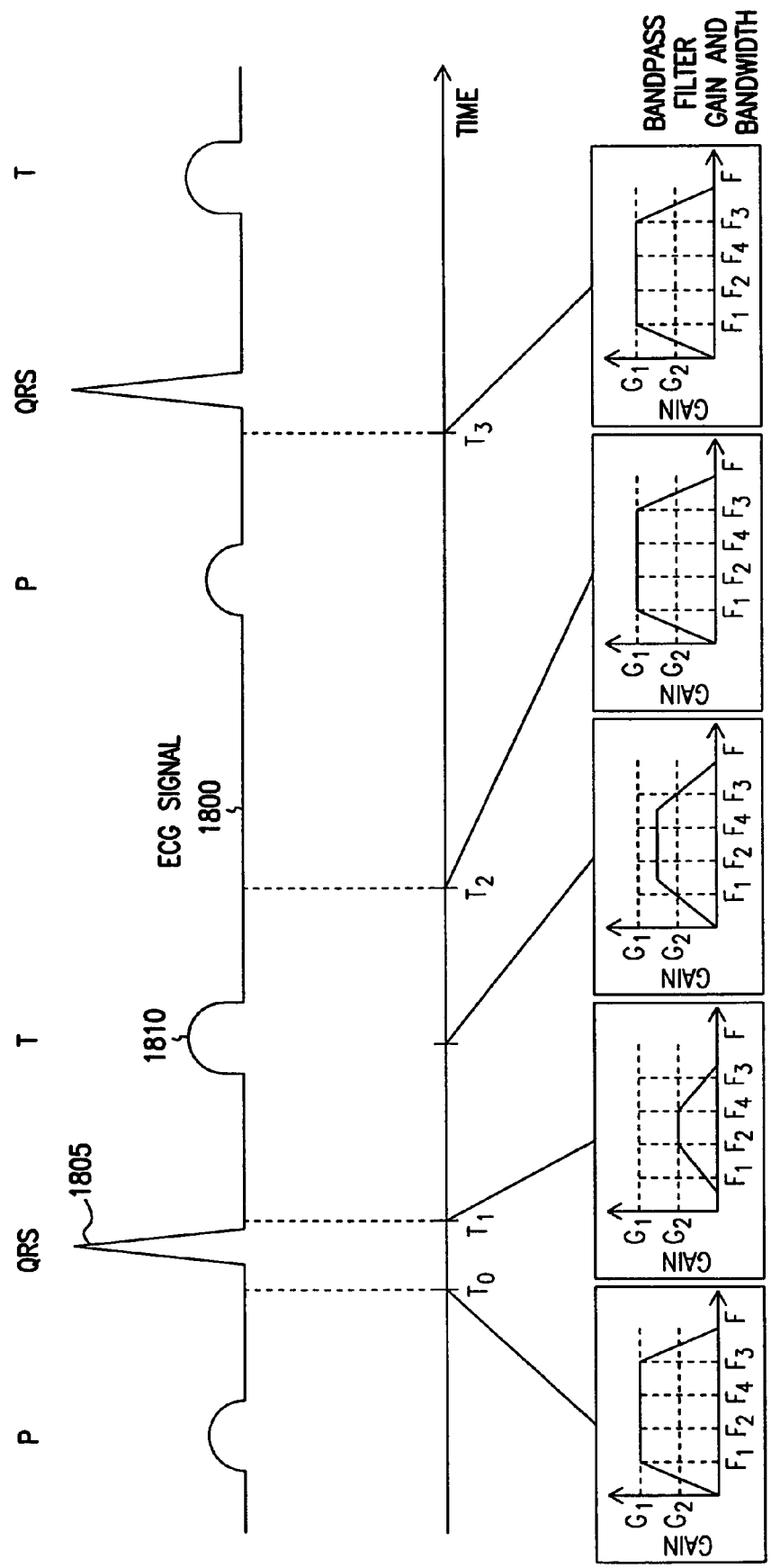
FIG. 19 is a signal flow graph, corresponding to the flow chart of FIG. 17, illustrating an intrinsic heart signal and frequency bandwidths of portions of the sensing circuit in which an event (e.g., a QRS complex) triggers a decrease in a passband bandwidth and gain, followed by a gradual increase in the passband bandwidth and gain during a period of time.

At step 1810 and time $t_2$, the highpass pole frequency of sensing circuit 210 decreases from $f_2$ back to $f_1$, the lowpass pole frequency of sensing circuit 210 increases from $f_4$ back to $f_3$, and the passband gain increases from $G_2$ to $G_1$. As a result, after the first time period $t_2$-$t_1$, such as during the time period $t_3$-$t_2$ sensing circuit 210 is made again more sensitive to T-waves. In one embodiment, the lowpass and highpass pole frequencies and the passband gain are switched at time $t_1$, and switched back at time $t_2$. In another embodiment, the lowpass and highpass pole frequencies and passband gain are switched at time $t_1$, and then gradually returned toward their original values during the first time period $t_2$-$t_1$, as illustrated in FIG. 19. In this embodiment, both the gain and the bandwidth of the frequency response are time dependent during the time period $t_2$-$t_1$.

FIG. 20 is a signal flow graph, similar to FIG. 19, illustrating the case of step 1800 in which therapy, such as a pacing stimulation, is delivered at time $t_1$, thereby evoking QRS complex 1805, and initiating the adjustment in the gain and frequency response of sensing circuit 210 to make the sensing circuit less sensitive to T-wave 510 during the first time period $t_2$-$t_1$. Although FIGS. 18-20 illustrate using the same time period for adjusting the gain and bandwidth, it is understood that different time periods can be used for adjusting the gain and bandwidth. For example, an event can trigger a first time period over which the frequency bandwidth is reduced, and also trigger a second time period, different from the first time period, over which the gain is reduced.

CONCLUSION

The above-described system provides, among other things, a cardiac rhythm management system with a time-dependent frequency response for sensed heart signals. A change in the frequency response is triggered by a sensed or evoked event to make it less sensitive to the detection of a subsequent event for a period of time. This provides better discrimination between particular events included in a heart signal so that appropriate therapy can be delivered to the patient based such events.

It is to be understood that the above description is intended to be illustrative, and not restrictive. Although particular embodiments have been described, combinations of such embodiments are understood to be included within the scope of the invention. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm monitoring or management system, including:
   a sensing circuit configured for sensing an intrinsic electrical heart signal, the sensing circuit having a frequency response that is time-dependent during a first time period initiated by at least one of a detected pacing therapy event or a detected evoked or detected intrinsic heart chamber contraction event of the heart signal, the sensing circuit configured to trigger a frequency response that is temporarily less sensitive to detecting evoked and intrinsic events of the heart signal followed by gradual adjustment of a frequency bandwidth of the frequency response as a function of an elapsed time relative to the event such that the frequency response gradually becomes more sensitive to detecting evoked and intrinsic heart chamber contraction events of the heart signal, the elapsed time measured or received by the sensing circuit during the same cardiac cycle as the event, to restore the frequency response within a time period of less than or equal to 500 milliseconds such that the frequency response is restored during the same cardiac cycle as the event.

2. The system of claim 1, in which the sensing circuit is configured to trigger the adjustment in response to the detected evoked heart chamber contraction event and also in response to the detected intrinsic heart chamber contraction event.

3. The system of claim 1, in which the sensing circuit is configured such that the frequency response includes a bandwidth that is time-dependent for the first time period, and the first time period is initiated by at least one of the detected pacing therapy event, a detected evoked QRS complex of the heart chamber contraction of the heart signal, or a detected intrinsic QRS complex of the heart chamber contraction of the heart signal.

4. The system of claim 3, in which the sensing circuit is configured such that the bandwidth decreases to a second bandwidth value, from a first bandwidth value, upon occurrence of the event.

5. The system of claim 4, in which the sensing circuit is configured such that the bandwidth increases from the second bandwidth value toward the first bandwidth value during the first time period.

6. The system of claim 5, in which the sensing circuit is configured such that the bandwidth includes a passband.

7. The system of claim 6, in which the sensing circuit is configured such that an attenuation of a T-wave of the heart signal by the frequency response of the first sensing circuit during the first time period is greater than or equal to the attenuation of the T-wave immediately after expiration of the first time period.

8. The system of claim 7, in which the sensing circuit is configured such that the first time period is greater than or equal to 250 milliseconds.

9. The system of claim 8, in which the sensing circuit is configured such that the first time period is approximately between 250 milliseconds and 500 milliseconds.

10. The system of claim 8, in which the sensing circuit is configured such that the first time period is approximately 500 milliseconds.

11. The system of claim 10, in which the sensing circuit includes an automatic gain control (AGC) circuit.

12. The system of claim 1, in which the sensing circuit is configured such that a highpass pole frequency of the frequency response is time-dependent for the first time period, and the first time period is initiated by at least one of the detected pacing therapy event and detected evoked and detected intrinsic heart chamber contraction events of the heart signal.

13. The system of claim 12, in which the sensing circuit is configured such that the first time period is initiated by at least one of the detected pacing therapy event and detected evoked and detected intrinsic QRS complexes of the heart chamber contraction, and the highpass pole frequency increases to a second frequency value, from a steady-state first frequency value, in response to detection of the detected pacing therapy event or a QRS complex of the heart chamber contraction.

14. The system of claim 13, in which the sensing circuit is configured such that the highpass pole frequency gradually decreases from the second frequency value toward the first frequency value during the first time period.

15. The system of claim 1, in which the sensing circuit is configured such that a lowpass pole frequency is time-dependent for the first time period, and the first time period is initiated by at least one of the detected pacing therapy event and detected evoked and detected intrinsic heart chamber contraction events of the heart signal.

16. The system of claim 15, in which the sensing circuit is configured such that the first time period is initiated by at least one of the detected pacing therapy event and detected evoked and detected intrinsic QRS complexes of the heart chamber contraction, and the lowpass pole frequency decreases to a second frequency value, from a first frequency value during the first time period.

17. The system of claim 16, in which the sensing circuit is configured such that the first time period is initiated by at least one of the detected pacing therapy event and detected evoked and detected intrinsic QRS complexes of the heart chamber contraction, and the lowpass pole frequency gradually increases from the second frequency value toward the first frequency value during the first time period.

18. The system of claim 1, in which the sensing circuit includes a gain that is time-dependent during a second time period initiated by at least one of the pacing therapy event or the evoked or intrinsic event of the heart signal.

19. The system of claim 18, in which the sensing circuit is configured such that the second time period is initiated by at least one of the detected pacing therapy event and the detected evoked and detected intrinsic heart chamber contraction event of the heart signal.

20. The system of claim 19, in which the sensing circuit is configured such that the gain decreases to a second gain value, from a first gain value, during the second time period.

21. The system of claim 20, in which the sensing circuit is configured such that the gain gradually increases, from the second gain value toward the first gain value during the second time period.

22. The system of claim 1, wherein the gradual adjustment of the frequency bandwidth comprises a substantially continuous function of the elapsed time.

23. The system of claim 1, wherein the first time period is initiated by the detected pacing therapy event.

24. The system of claim 1, wherein the first time period is initiated by the detected evoked heart chamber contraction event of the heart signal.

25. The system of claim 1, wherein the first time period is initiated by the detected intrinsic heart chamber contraction event of the heart signal.

26. A cardiac rhythm management system, including:
an electronics unit including:
a therapy circuit;
a sensing circuit configured for sensing an intrinsic heart signal of a heart; and
a bandpass filter, included in the sensing circuit, the filter having a frequency response that is time-dependent during a first time period initiated by one of a detected pacing therapy event or a detected evoked or detected intrinsic heart chamber contraction event of the heart signal and the sensing circuit configured to trigger a frequency response that is temporarily less sensitive to detecting evoked and intrinsic events of the heart signal followed by gradual adjustment of a frequency bandwidth of the frequency response as a function of an elapsed time relative to the event such that the frequency response gradually becomes more sensitive to detecting evoked and intrinsic heart chamber contraction events of the heart signal, the elapsed time measured or received by the sensing circuit during the same cardiac cycle as the event, to restore the frequency response within a time period of less than or equal to 500 milliseconds such that the frequency response is restored during the same cardiac cycle as the event; and
a leadwire, coupled to the electronics unit and configured to be coupled to a portion of the heart; and
a programmer, remote from and communicatively coupled to the electronics unit, the programmer including a parameter controlling one of: (a) the frequency response of the bandpass filter, and (b) the duration of the first time period.

27. The system of claim 26, in which the sensing circuit further includes a gain that decreases from a first gain value to a second gain value during a second time period initiated by one of the detected pacing therapy event or the detected evoked or detected intrinsic event of the heart signal.

28. The system of claim 26, wherein the gradual adjustment of a frequency bandwidth comprises a substantially continuous function of the elapsed time.

29. The system of claim 26, wherein the first time period is initiated by the pacing therapy event.

30. The system of claim 26, wherein the first time period is initiated by the detected evoked heart chamber contraction event of the heart signal.

31. The system of claim 26, wherein the first time period is initiated by the detected intrinsic heart chamber contraction event of the heart signal.

* * * * *